United States Patent [19]

Lewis et al.

[11] Patent Number: 5,091,626

[45] Date of Patent: Feb. 25, 1992

[54] METHOD FOR THE ABLATIVE RESHAPING OF MATERIAL SURFACES

[75] Inventors: Aaron Lewis, Jerusalem; Amihay Fuxbruner, Ramat-Gan; Itzhak Hemo, Kiryat Yovel, all of Israel

[73] Assignees: Hadassah Medical Organization; Israel Yissum Research Development Company of the Hebrew University of Jerusalem, both of Jerusalem, Israel

[21] Appl. No.: 473,814

[22] Filed: Feb. 2, 1990

[51] Int. Cl.$^5$ .............................................. B23K 26/00
[52] U.S. Cl. ................................................. 219/121.69
[58] Field of Search ....................... 219/121.68, 121.69

[56] References Cited

U.S. PATENT DOCUMENTS

| | | | |
|---|---|---|---|
| 4,114,018 | 9/1978 | Von Allmen et al. | 219/121.69 X |
| 4,724,522 | 2/1988 | Belgorod | 128/303.1 X |
| 4,842,782 | 6/1989 | Portney et al. | 264/1.4 |
| 4,909,818 | 3/1990 | Jones | 219/121.68 X |

*Primary Examiner*—C. L. Albritton
*Attorney, Agent, or Firm*—Leydig, Voit & Mayer

[57] ABSTRACT

A method for the ablative reshaping of material surfaces, including the steps of providing a source of an ablative beam having a given average fluence distribution over its cross-sectional extent, determining the ablation curve of the material to be reshaped, selecting, from said ablation curve, an ascending region having an at least approximately constant slope, selecting a beam fluence from among the fluences comprised in said region, irradiating the material surface to be shaped, and controlling the geometry of the material surface thus being reshaped by controlling the total amount of energy per unit area of said surface delivered during said irradiation.

6 Claims, 5 Drawing Sheets

METHOD FOR THE ABLATIVE RESHAPING OF MATERIAL SURFACES

The present invention relates to a method for the ablative reshaping of material surfaces using an ablative beam that has a varying fluence distribution over its cross-sectional extent.

Studies on the interaction of excimer laser radiation with organic polymers led to the discovery, several years ago, that it was possible to ablate many polymers and biological tissues with little deposition of heat using pulses from the argon fluoride (ArF) excimer laser which emits in the far UV at 193 nm. At this wavelength the photon has an energy of 6.4 eV and since many organic materials have a bond strength that is estimated between 4–5 eV, it was suggested that direct photochemical bond breaking is the mechanism for the observed ablation of proteins by the 193 nm, 10–20 nsec pulses of the ArF laser. Later it was discovered that it was possible to ablate the same materials using other wavelength of the excimer laser such as 248 nm, 308 nm and 351 nm.

L'Esperance et al (Arch. Opthalmol. Vol. 7, January 1989, pp. 131-139) have described a system according to which a modified beam from an ArF excimer laser is used to reprofile the human cornea by removing, one after another, utilizing the above ablation effect, successive concentric zones of the tissue, until the desired shape is approximated. L'Esperance et al, being conscious of the fact that the laser beam issuing from the source has a varying, in fact nearly Gaussian, distribution over its cross-sectional extent, invests a considerable effort, by way of instrumentation, in "rectifying" this variance, the outcome of which effort is a beam of still not perfect uniformity of fluence over its cross section, which imperfection must be further compensated for by rotating the beam about its axis. The tissue to be etched is then exposed zone by concentric zone, using an indexable wheel comprising a set of apertures or stops and varying exposure time (or number of pulses) for each stop according to the ablation depth required at each zone. However, due to the finite number of stops, transition, in the finished surface, between zones is step-like rather than smooth.

It having been surprisingly found that Gaussian fluence distribution which the above summarized prior art has laboriously attempted to eliminate, is in fact the very distribution that would produce paraboloidal surfaces (for circular lenses) or parabolic surfaces (for cylindrical lenses), it is one of the objects of the present invention to overcome the drawbacks of the prior art and to provide a method for the ablative shaping or reshaping of material surfaces, using an ablative beam that has a varying fluence distribution over its cross-sectional extent, a method that does not require aperturing the beam and in which the entire surface is ablated simultaneously, producing a continuous, smooth surface.

According to the present invention, this is achieved by providing a method for the ablative reshaping of material surfaces, comprising the steps of providing a source of an ablative beam having a given average fluence distribution over its cross-sectional extent, determining the ablation curve of the material to be reshaped, selecting, from said ablation curve, an ascending region having an at least approximately constant slope, selecting a beam fluence from among the fluences comprised in said region, irradiating the material surface to be reshaped, and controlling the geometry of the material surface thus being reshaped by controlling the total amount of energy per unit area of said surface delivered during said irradiation.

The invention will now be described in connection with certain preferred embodiments with reference to the following illustrative figures so that it may be more full understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
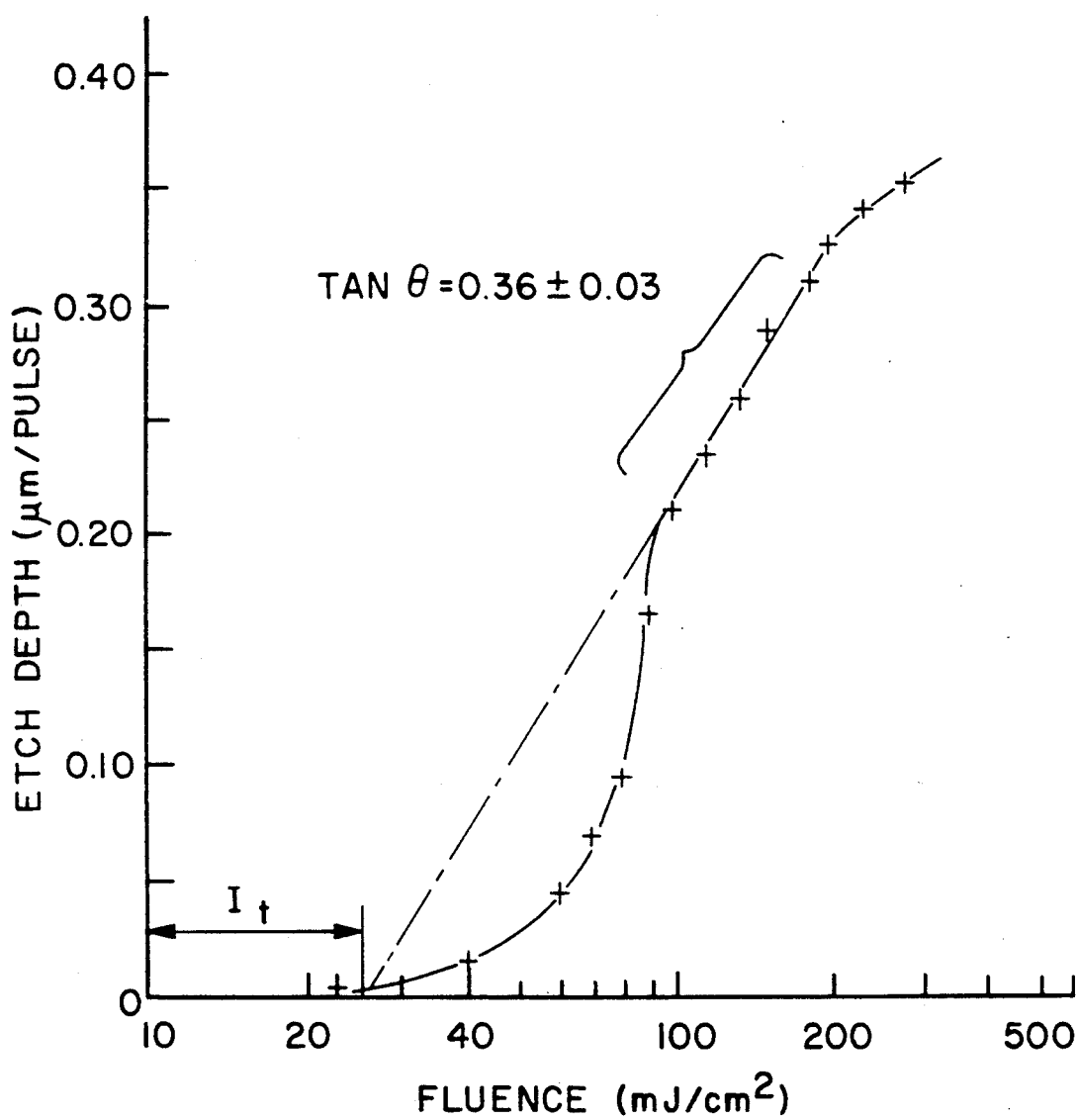
FIG. 1 represents the ablation curve for Perspex (PMMA), indicating etching depth as a function of fluence.
Figure 2:
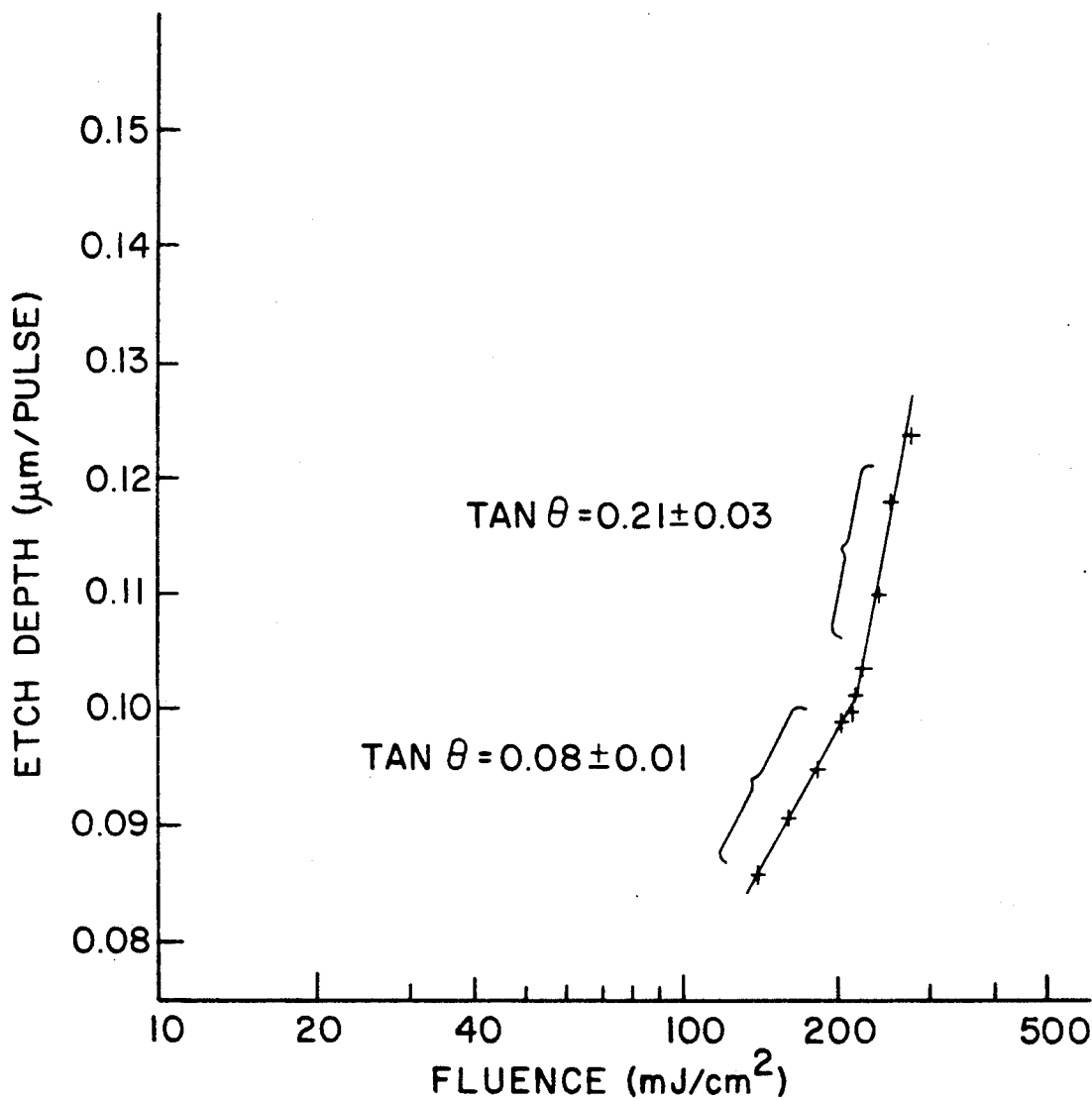
FIG. 2 is a similar diagram, relating to polycarbonate.

The following is the theoretical model on which the method according to the invention is based. Underlying the model are two basic assumptions:

1) The average fluence I impacting the surface of a workpiece to be reshaped (see detailed definitions further below), is assumed to have an at least approximately Gaussian distribution over its cross-sectional extent, such that the mathematical function describing the difference between the final surface and the initial surface defines a paraboloid or parabolic surface (for circular and cylindrical lenses, respectively);

2) The ablation curve (etch depth per pulse or per unit time vs. log of fluence) of the material to be ablated has an ascending region of constant slope, the range of fluences used being located within this region (see FIGS. 1 and 2.)

The average fluence distribution, given its Gaussian nature, is $$I(r) = A\exp(-r^2/2\sigma^2), \quad (1)$$

where A and $\sigma^2$ are constants and $\sigma^2$ can have either positive or negative values, with r being the independent variable (either in polar coordinates for producing the paraboloid differences, or in Cartesian coordinates for producing the parabolic cylindrical differences).

With these assumptions, after one pulse or one second (for a continuous source), the beam will reshape the surface of the workpiece and the function describing the difference between the final surface and the initial surface is given by $Z(r) = 1/\alpha \ln I/I_t$, with I being the fluence distribution applied to the workpiece at that pulse or time, and $I_t$ the intercept, on the x-axis of the ablation curve, of the selected curve region (FIG. 1).

After p pulses or seconds, $$Z(r) = p/\alpha \ln I/I_t \qquad (2)$$

The profile of the surface can be obtained by substituting equation (1) into equation (2), yielding $$Z(r) = -(\tfrac{1}{2}R)r^2 + B \qquad (3)$$

where $$R = \alpha\sigma^2/p \qquad (4)$$

and $$B = p/\alpha \ln A/I_t. \qquad (5)$$

The result of this substitution shows that the function Z(r) describes a parabolic surface or a parabolic cylindrical surface where the radius of curvature is given by R.

Thus, if the material on which this parabolic difference is impressed has an initial radius of curvature ($R_i$), a new surface is formed with a final radius of curvature ($R_f$) which is given by $$1/R_f = 1/R + 1/R_i \qquad (6)$$

By substituting R from (4) into (6) one obtains $$1/R_f = (1/\alpha\sigma^2)p + 1/R_i \qquad (7)$$

Since n, $\alpha$, and $\sigma^2$ are constants, the result is a linear relation between $1/R_f$ and the number of pulses, or time.

The constant $\sigma^2$ which appears in the Gaussian description of the beam (equation 1) can now be expressed in terms of the properties of the materials on which the parabolic difference is to be impressed. Thus for two materials labelled 1 and 2

$$\sigma^2 = p_1 R_1/\alpha_1 = p_2 R_2/\alpha_2 \qquad (8)$$

and $$R_2 = (R_1 p_1 \alpha_2/\alpha_1)p_2. \qquad (9)$$

If the material on which this parabolic difference is impressed has an initial radius of curvature $R_1$ and the material is a lens with an initial dioptric power $D_i$ and with an index of refraction of n, a new lens is formed with a final dioptric power $D_f$ which is given by $$D_f = D + D_i \qquad (10)$$

where $$D = 1/f_f - 1/f_i = (1-n)/R, \qquad (11)$$

where $f_i$ and $f_f$ are the initial and final focal length.

By substituting R from (4) into (11) we get $$D = [(1-n)/\alpha\sigma^2]p. \qquad$$

Since n, $\alpha$ and $\sigma^2$ are constants, a linear relation is seen to exist between the new dioptric power and the number of pulses or time:

$$D_f = -(1/\delta) + D_i \qquad (13)$$

where $$\delta = -\alpha\sigma^2/(1-n) = \text{constant}. \qquad (14)$$

The constant $\sigma^2$ which appears in the Gaussian description of the beam (equation 1) can now be expressed in terms of the properties of the materials on which the parabolic pattern is to be impressed. Thus, for two materials labelled 1 and 2

$$\sigma^2 = -\delta_1(1-n_1)/\alpha_1 = -\delta_2(1-n_2)/\alpha_2 \qquad (15)$$

$$(1-n_1)\tan\theta_1/(1-n_2)\tan\theta_2 = \delta_2/\delta_1 \qquad (16)$$

where $\tan\theta = 1/\alpha \log e$ is the slope of the ablation curve.

In summary, the conclusions to be drawn from the model are that it is possible to reshape material surfaces in such a way that the mathematical function which describes the difference between the final surface and the initial surface defines an at least approximately paraboloid or parabolic surface. More specifically, if the initial surface has a given initial radius of curvature, then it is possible to change the radius of curvature in a controlled fashion by simply varying the number of pulses or the time used to irradiate the workpiece: 1/R linearly depends on the number of pulses or on time, as emerges from equation 7 in the above.

It is furthermore possible to predict the new radius of curvature of the surface formed in a second material, if a first material is used as a reference and equation 9 is applied to calculate $r_2$ from the term ($R_1 p_1 \alpha_2/\alpha_1$).

As $D_f$, too, linearly depends on the number of pulses or on the time, it is similarly possible to change the dioptric power of a lens having an initial dioptric power $D_i$ (see equation 13). Also, the new dioptric power $D_f$ can be predicted for a second material, if a first material is used as reference and equation 16 is applied to establish $\delta_2$ for the second material.

As mentioned before, the method according to the invention can be applied with a pulsed source as well as with a continuous source.

For ablation with a pulsed source, the average fluence distribution I(r) as applied to the workpiece and generalized in equation 1, is given by $$I(\vec{r}) = (I_1(\vec{r}) \times I_2(\vec{r}) \times \ldots I_p(\vec{r}))^{1/p},$$

where $I_1(\vec{r}), I_2(\vec{r}), \ldots$ is the fluence distribution applied to the workpiece at the nth pulse and p is the number of pulses. It should be remembered that all fluences used must be located within the regions of constant slopes of the ablation curves.

For ablation with a continuous source, the average fluence distribution I(r) as applied to the workpiece and generalized in equation 1, is given by $$I(\vec{r}) = \exp(1/p \int_0^p \ln I(r,t)dt)$$

where I(r,t) is the fluence distribution applied to the workpiece at the time t, and p is the irridation time.

When $\sigma^2$ is positive—the change of the radius of curvature and the dioptric power are negative. When $\sigma^2$ is negative, the above magnitudes are positive.

Figure 4:
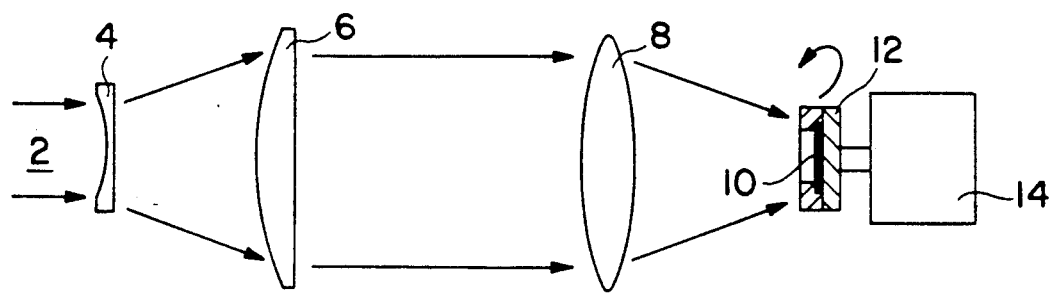
FIG. 4 shows an essential part of the instrumental set-up involved.

It should be stressed that, as the fluence distribution of the laser beam, through basically Gaussian, is not perfectly symmetrical about the center of the beam, it must be averaged in order to obtain workpieces of perfect geometry. This is achieved by producing a relative rotational movement between the beam and the workpiece. The simplest solution to this problem is to rotate the workpiece by means of an electric motor, as seen in FIG. 4. When this is not feasible, such as in envisioned in-vivo treatments of the human cornea, the same result is, of course, obtained by rotating the beam, which is easily done with a mirror arrangement.

FIG. 1 represents the ablation curve for Perspex (PMMA), indicating the etching depth (μm/pulse) as a function of fluence (mJ/cm$^2$). Seen is also the useful region of the curve, the slope of which (on semilogarithmic paper) is constant (tan $\theta = 0.36 \pm 0.03$). $I_t$ is the x-axis intercept of the above useful region.

Another ablation curve is shown in FIG. 2 and relates to polycarbonate. It is seen that the curve for this material has two useful regions, one with tan $\theta = 0.08 \pm 0.01$, the other with tan $\theta = 0.21 \pm 0.03$.

Figure 3:
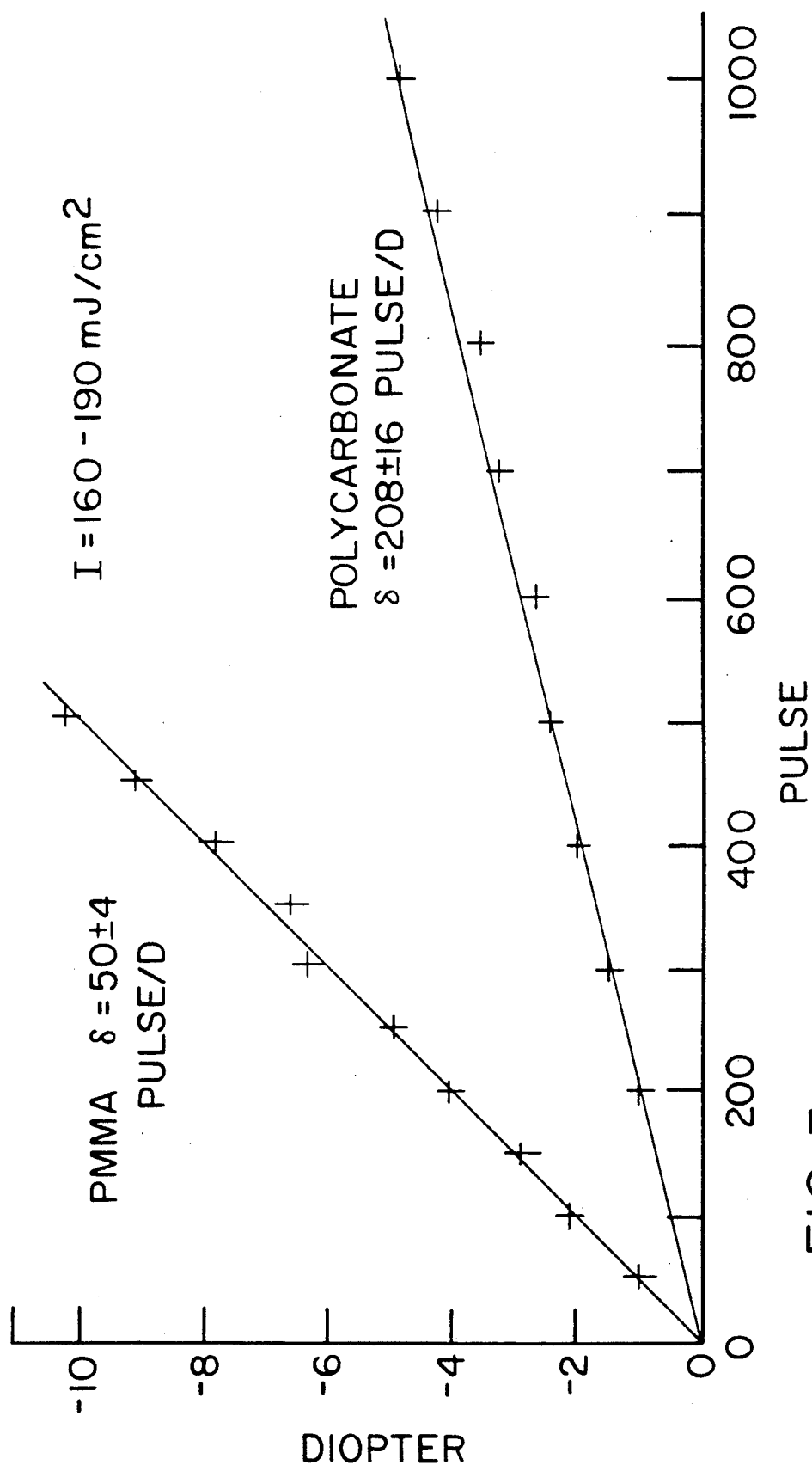
FIG. 3 illustrates lens power as a function of the number of laser pulses applied.

FIG. 3 illustrates the power of lenses as a function of the number of laser pulses applied. It is seen that at an average fluence distribution of 160-190 mJ/cm$_2$, Perspex requires $=50\pm 4$ pulses for a changer of 1 dioptre, while polycarbonate requires $208 \pm 16$ pulses for the same change.

FIG. 4 is a schematic representation of the optical arrangement which is an essential part of the instrumental setup involved in carrying out the method according to the invention. There is seen the laser beam 2 coming from the source (not shown). At this point, the beam has a rectangular cross section which, for the particular laser used, is 22×6 mm. In order to satisfy the above-mentioned basic assumptions, the beam is expanded with the aid of a negative cylindrical lens 4 and collimated by a positive cylindrical lens 6 to a square cross section of 22×22 mm. A positive spherical lens 8 is then used to cause the modified beam to converge onto the workpiece 10 attached to a mounting 12 mounted on the shaft of an electric motor 14. This set-up permits the workpiece to carry out the essential fluence-averaging movement mentioned earlier. To produce cylindrical lenses of greater length, an arrangment might be necessary that produces a relative translatory movement between workpiece and beam.

Figure 5:
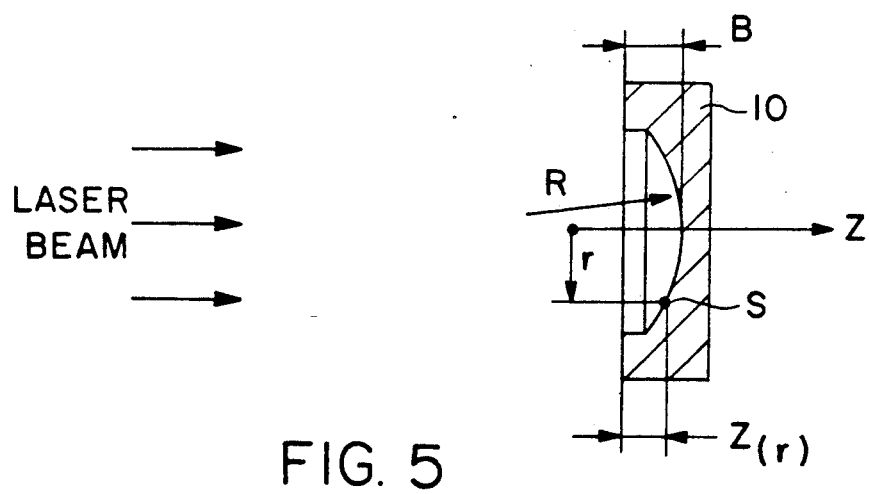
FIG. 5 represents a workpiece, including part of the notation used.

FIG. 5 illustrates a workpiece 10 as well as part of the notation used in the above explanation of the method. Seen is the Z-axis, the radius of curvature R, the central ablation depth B and a point S with its coordinates r and Z(r).

Figure 6C:
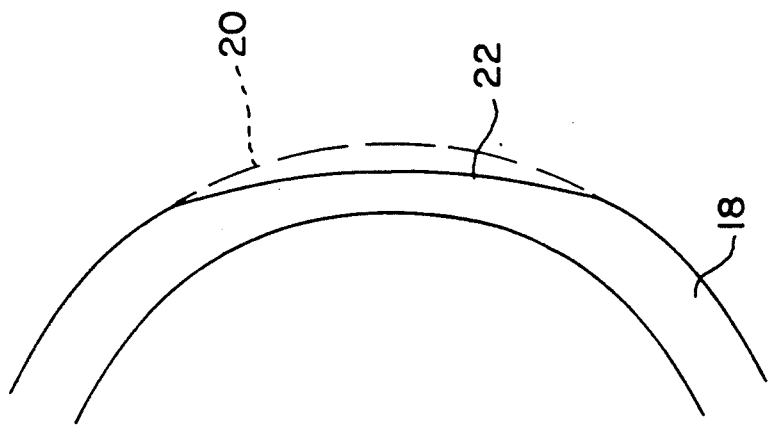
FIGS. 6a–6c illustrate the application of the method according to the invention in an opthalmologic procedure aimed at reshaping parts of the human cornea.

FIG. 6 schematically illustrates an important application of the method according to the invention, which relates to recontouring parts of the human cornea to remedy problems of refraction.

Figure 6B:
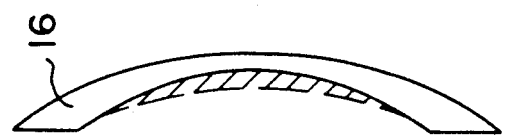
Figure 6A:
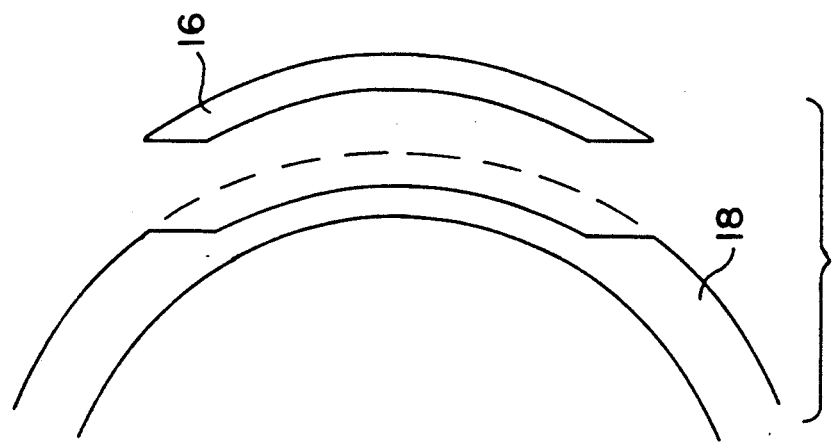

In a surgical procedure known as keratomileusis, a corneal button 16 is lifted off the cornea 18 (FIG. 6A). The present method is then used to reshape this button as shown in FIG. 6B, where the shaded portion indicates the removed material. This modified corneal button is then resutured back into position as an autograft (FIG. 6C), being somewhat flattened in the process and resulting in a reduction of dioptric power. The original surface 20 is indicated by a dashed line, with the modified surface 22 shown by a solid line.

Although the distribution utilized in the present method as detailed in the above was inherently Gaussian, it is similarly possible to make use also of distributions which, inherently or after manipulation, are non-Gaussian, and facilitate production of other than paraboloid or parabolic surfaces.

While the present invention was explained in conjunction with an ArF laser, it should be appreciated that other lasers, too, could be used. Furthermore, it is also possible to use sources other than electromagnetic radiation such as ion beams or jets of fluids and/or gases such as HF.

It will be evident to those skilled in the art that the invention is not limited to the details of the foregoing illustrative embodiments and that the present invention may be embodied in other specific forms without departing from the spirit or essential attributes thereo. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for the ablative reshaping of material surfaces, comprising the steps of:
   providing a source of an ablative beam having a given average fluence distribution over its cross-sectional extent;
   determining the ablation curve of the material to be reshaped;
   selecting, from said ablation curve, an ascending region having an at least approximately constant slope;
   selecting a beam fluence from among the fluences comprised in said region;
   irradiating the material surface to be reshaped, and
   controlling the geometry of the material surface thus being reshaped by controlling the total amount of energy per unit area of said surface delivered during said irradiation.

2. The method as claimed in claim 1, wherein said distribution is at least approximately Gaussian.

3. The method as claimed in claim 1, wherein said source is a pulsed source.

4. The method as claimed in claim 1, wherein said source is a continuous source.

5. The method as claimed in claim 1, further comprising the step of producing, during said irradiation, a relative rotational movement between said beam and said material surface.

6. The method as claimed in claim 1, further comprising the step of producing, during said irradiation, a relative translatory movement between said beam and said material surface.

* * * * *